United States Patent [19]

Boulanger

[11] Patent Number: 5,665,082

[45] Date of Patent: Sep. 9, 1997

[54] HIGHLY ABSORBENT TRANSFER LAYER STRUCTURE

[75] Inventor: Roger Boulanger, Ste-Julie, Canada

[73] Assignee: Johnson & Johnson Inc., Canada

[21] Appl. No.: 548,344

[22] Filed: Nov. 1, 1995

[51] Int. Cl.$^6$ .................... A61F 13/15; A61F 13/20
[52] U.S. Cl. .................... 604/365; 604/378; 604/381; 428/103
[58] Field of Search .................... 604/358, 365–366, 604/372, 378, 381–382, 385–1; 428/103, 236–237, 290, 302

[56] References Cited

U.S. PATENT DOCUMENTS 3,828,783  8/1974  Kennette et al. .................... 604/366
3,934,588  1/1976  Mesek et al. .................... 604/365
4,050,463  9/1977  Schaar .................... 604/366
4,129,132  12/1978  Butterworth et al. .................... 604/366
5,378,528  1/1995  Makoui .................... 604/365

FOREIGN PATENT DOCUMENTS 2 082 643  3/1982  United Kingdom .................... 604/379

*Primary Examiner*—P. Zuttarelli
*Attorney, Agent, or Firm*—James P. Barr

[57] ABSTRACT

A transfer layer of cellulosic air-laid material characterized by a non-uniform binder distribution profile that allows a faster liquid acquisition. In a specific example, the transfer layer has a higher concentration of binder on its liquid-acquisition surface than on the liquid-release surface. Typically, the liquid-release surface of the transfer layer forms part of the interface transfer layer/absorbent core in the structure for absorbing body exudate.

19 Claims, 1 Drawing Sheet

HIGHLY ABSORBENT TRANSFER LAYER STRUCTURE

FIELD OF THE INVENTION

The present invention relates to the art of manufacturing structures for handling body exudate. More particularly, the invention relates to a binder consolidated liquid-absorbent article characterized by a non-uniform binder distribution profile that allows the liquid-absorbent article to take-up liquid faster. The liquid-absorbent article is well suited for use as a transfer layer in a sanitary napkin or another disposable sanitary protection product. The invention also relates to a method for manufacturing the novel liquid-absorbent article.

BACKGROUND OF THE INVENTION

Sanitary napkins are multi-layered structures that normally comprise a body contacting liquid-pervious cover layer, an absorbent system and a barrier layer that prevents fluid entrapped in the absorbent system to egress from the garment facing surface of the sanitary napkin. Usually, the absorbent system is a dual-layer arrangement. It includes an absorbent core whose primary function is to entrap the liquid discharge permanently and a transfer layer whose function is to collect the body exudate quickly and then meter the liquid to the absorbent core. Liquid discharged on such composite absorbent systems will rapidly ingress the transfer layer due to its highly porous network. From the transfer layer, liquid migrates toward the absorbent core by capillary pressure because of the substantial difference in wicking power between the different materials. The liquid migration is well-controlled, occurring at the rate of acceptance of the absorbent core.

The transfer layer is in the form of a sheet and it is typically made from cellulosic fibers by an air-laid process. To consolidate the porous sheet so that it can withstand the mechanical stresses normally encountered in use, without suffering a loss of structural integrity, binder is applied on both main surfaces of the transfer layer, namely on its liquid-acquisition surface that faces the cover layer and on its liquid-release surface oriented toward the absorbent core. The amount of binder applied to both surfaces is the same.

Conventional wisdom dictates that from the point of view of liquid absorption performance, the presence of binder on the transfer layer is undesirable. The binder sites that link the fibers are thought to behave as local barriers preventing liquid from freely migrating in and within the porous structure. The requirement of fast liquid penetration is particularly important for the liquid-acquisition surface of the transfer layer that should be able to take-up rapidly large amounts of liquids. Otherwise, the sanitary napkin may fail due to overflow leakage at the transfer layer level.

OBJECTS AND STATEMENT OF THE INVENTION

An object of the present invention is a binder-consolidated liquid-absorbent article manifesting a short liquid-penetration time.

Another object of the invention is a method for manufacturing the aforementioned liquid-absorbent article.

As embodied and broadly described herein, the invention provides an integrally formed liquid-absorbent article of particulate material including first and second zones in intimate fluid communicative relationship, each zone having a multiplicity of inter-particle interstices admitting passage of liquid, whereby liquid contained in one of said zones can migrate toward the other of said zones, said liquid-absorbent article containing binder, said first zone having a higher average concentration of binder than said second zone.

For the purpose of this specification "particle" means a small unit of material without limitation of shape. A fiber that is characterized by a geometrical extension along a preferential direction will be considered a particle. Therefore, "particle" and "particulate" cover a material made of fibers, particles having non-fibrous identity, such as sphagnum moss, or a combination of both. Also, the term "absorbent" will be used to designate a structure capable of taking-up liquid, without any regard to liquid-retentivity. As such, a material well suited for use as a transfer layer, such as a low density cellulose web, will be considered "absorbent" although the material has poor liquid-retentivity characteristics, i.e., it is designed specifically to allow liquid to easily egress its porous structure so the liquid can transfer itself to the absorbent core. Finally, "binder concentration" means the weight of binder (solids) per unit weight of particulate material and other constituents that may be included with the particulate material but excluding the binder (solids). The "average concentration of binder" for a given zone is obtained by dividing the weight of binder (solids) contained in the zone by the weight of the zone (solids) from which the weight of binder has been subtracted.

Without intent of being bound by a specific theory, the present inventor believes that the non-uniform binder distribution profile creates within the liquid-absorbent article an intermediate zone having a high void volume (low density). Liquid migrating through the porous network of the liquid-absorbent article will have a tendency to spread along the X-Y plane, once it reaches the high void volume zone. The liquid front, now distributed over a larger surface area advances more rapidly since it is channelled through a larger number of capillary passageways. Such liquid-absorbent structure is particularly useful as a transfer layer for a disposable absorbent product, such as a sanitary napkin, diaper, adult incontinence brief, urinary pad, wound dressing and nursing pad. In normal use, the body exudate discharged over the disposable absorbent product is limited to a small impact area. Prior art transfer layers are not designed to allow the advancing liquid front to expand laterally significantly. As a result, the liquid is constrained to flow through a comparatively small number of capillaries. In contrast, the novel liquid-absorbent structure induces the liquid front to flow laterally and also in the Z direction (along the thickness of the liquid-absorbent article). This feature enables the liquid to travel faster.

Surprisingly, the liquid-absorbent article manifests a higher liquid penetration rate when the liquid is deposited on the surface on which the binder concentration is highest. This is contrary to conventional wisdom that dictates that an increase in the amount of binder on the liquid-acquisition surface of a porous structure reduces the rate of penetration of liquid in the structure.

In a preferred embodiment, the liquid-absorbent article according to the invention is made of fibers. Cellulosic fibers are most preferred although other fibers could also be used without departing from the spirit of the invention. The length of the fibers influences the formation of the intermediate high void volume zone. Best results have been obtained with fibers having a length not exceeding 3.5 millimeters (mm).

As embodied and broadly described herein, the invention also provides a transfer layer for a disposable absorbent article, said transfer layer including particles defining a multiplicity of inter-particle interstices admitting passage of liquid, said transfer layer including a liquid-acquisition surface through which liquid can ingress said transfer layer and a liquid-release surface through which liquid can egress said transfer layer, said transfer layer containing binder, a concentration of binder in a vicinity of one of said surfaces being lower than in a vicinity of the other of said surfaces.

As embodied and broadly described herein, the invention also provides a method for manufacturing a binder consolidated liquid-absorbent article, said method comprising the steps of:

forming particulate material into a sheet having first and second main faces, said sheet having a multiplicity of inter-particle interstices admitting passage of liquid; and applying binder to said sheet to provide a higher concentration of binder in a vicinity of said first main face than a concentration of binder in a vicinity of said second main face.

In a most preferred embodiment, the liquid-absorbent article is manufactured from cellulosic fibers by the well-known air-laid process. Different quantities of binder are deposited on the opposite main surfaces of the cellulosic sheet to provide a non-uniform binder distribution profile. The liquid-absorbent article is then processed according to known techniques to incorporate it in a disposable absorbent product, such as a sanitary napkin.

DESCRIPTION OF A PREFERRED EMBODIMENT

The present invention provides an integrally formed liquid-absorbent article suitable for use as a transfer layer in a sanitary absorbent product, such as a sanitary napkin. The liquid absorbent article is characterized by a non-uniform binder deposition profile. In an exemplary embodiment, the transfer layer is manufactured in a sheet form from cellulosic fibers according to the well-known air-laid process. The resulting sheet is subjected to binder treatment that consists of spraying one main face of the sheet with binder, letting the binder set and then spraying the other face of the sheet with binder. The amount of binder deposited at each spraying step is different to create a higher binder concentration near one surface of the liquid-absorbent article than near the other surface.

Figure 1:
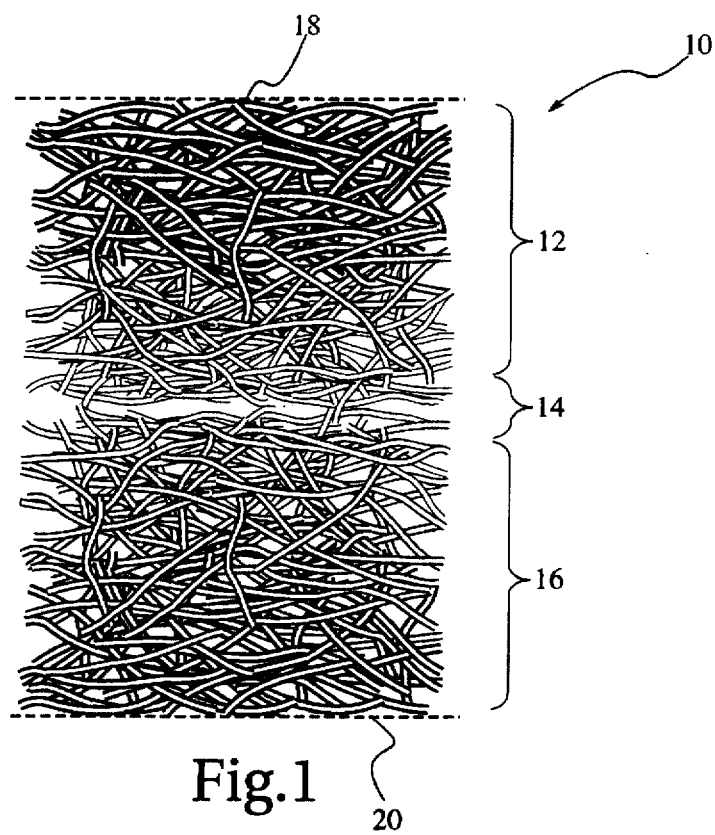
FIG. 1 is an enlarged cross-sectional view of a liquid-absorbent article according to the present invention.

FIG. 1 provides an enlarged cross-sectional view of the liquid-absorbent article designated comprehensively with the reference numeral 10. The liquid-absorbent article 10 includes three superposed layers, namely an upper layer 12, an intermediate layer 14 and a lower layer 16. The upper layer 12 and the lower layer 16 have approximately the same thickness, while the intermediate layer 14 is much thinner. The upper layer 12 is distinguished from the two other layers by a comparatively high binder content. The binder concentration profile is at a maximum level at the upper surface 18, where the binder has been deposited in liquid form by spraying. As depth increases, the binder concentration progressively diminishes toward the interface between the upper layer 12 and the intermediate layer 14, where virtually no binder exists. This negative binder concentration gradient is the result of a migration of the liquid binder substance that occurs immediately after the binder has been sprayed. The liquid binder sinks within the porous structure due to capillary pressure and gravity. However, the rate of progression of the liquid front gradually diminishes because the viscosity of the liquid increases as the curing process nears completion. The migration process is completed when the binder is fully cured.

The structure of the lower layer 16 is similar to the upper layer 12 except that it contains much less binder. The binder concentration of the lower layer 16 peaks at the lower surface 20 and gradually decreases in the upward direction until the interface lower layer 16/intermediate layer 14 where it drops to negligible levels.

Figure 2:
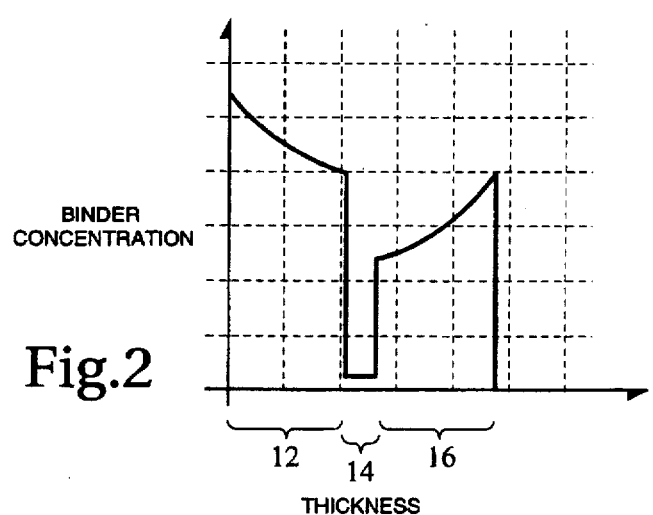
FIG. 2 is a graph illustrating the binder concentration in the liquid-absorbent article shown in FIG. 1.

The intermediate layer 14 is formed as a result of the presence of the binder consolidated upper and lower layers 12 and 16. Without intent of being bound by a particular theory it is believed that immediately after the binder is cured the fibers in the upper layer 12 and in the lower layer 16 are linked to one another and thus fixed in predetermined spacial positions, except the fibers at the intervening region between these two layers where the amount of binder is minimal. During subsequent manipulations and handling of the liquid-absorbent article, the layers 12 and 16 may slightly separate from one another creating between them the intermediate layer 14. The intermediate layer 14 is characterized by a much lower density (higher void volume) than layers 12 and 14 and it can transport liquid much faster than layers 12 and 14. The graph of FIG. 2 illustrates the binder deposition profile of the liquid-absorbent article 10.

When liquid is discharged on the liquid-absorbent article 10, say the surface 18, the liquid begins penetrating the porous network along a vector that is generally transverse to the plane of the liquid-absorbent article, i.e., the liquid front advances vertically and there is very little lateral dispersion. However, when the liquid reaches the intermediate layer 14, it spreads apart considerably and enters the lower layer 16 distributed over a larger surface area. The liquid travels faster through lower layer 16 because it is channelled through an increased number of capillary passageways.

In a specific example, the liquid-absorbent article 10 is made from cellulosic fibers (100% Southern Pine Kraft) by an air-laid process. The cellulosic web prior to the binder deposition has a basis weight of 66.2 grams per meter squared ($g/m^2$). The total amount of binder deposited on the cellulosic web ranges from about 10% to about 25% by weight of solids in the liquid-absorbent article (cellulosic fibers plus binder). In a preferred embodiment the amount of binder deposited on the cellulosic web is 13.8 $g/m^2$ of solids. EVA (ethylene vinyl acetate) binder has been found satisfactory. Acrylic binder can also be used. No less than 75% of the total amount of binder applied to the web is deposited on one surface of the web, while the balance (25% maximum) on the other surface. Most preferably, 85% of the total amount of binder (11.73 $g/m^2$ of solids in the example given above) is applied to one side of the web while the other side receives 15% (2.07 $g/m^2$). To effect the non-uniform binder deposition, the concentration of the liquid binder is changed, not the amount of material sprayed. Thus, both sides of the web receive the same amount of liquid, but the concentration of binder in the liquid varies. Other methods to effect the non-uniform binder deposition can also be used. For example, it could be considered to spray or otherwise deposit liquid binder having the same concentration on both faces of the web, except that one face receives more material than the other face.

The properties of the liquid-absorbent article 10 constructed under the specific example discussed above are compared with a control sample in a test. The control sample is identical to the invention except that the binder is applied uniformly on both surfaces of the cellulosic web. Thus each side receives 6.9 g/m$^2$ of binder (solids). The purpose of the test is to determine the capillary attraction developed by an absorbent material on a fluid.

The instrument disclosed in the U.S. Pat. No. 5,361,627 in the name of Johnson & Johnson Inc. issued on Nov. 8, 1994 is used for the test procedure. A sample of the material to be tested in the form of a rectangle 5 cm by 5 cm is laid on the sphagnum absorbent core taken from a sanitary napkin available in Canada under the brand name Stayfree Prima. The absorbent core acts as a source of capillary pressure to wick away liquid delivered on the sample. Three (3) cc of test fluid is deposited on the virgin sample and the sensor of the instrument is placed in contact with the absorbing surface of the sample. After 30 minutes from the fluid discharge the pressure reading in millimeters of mercury (mmHg) is recorded. Test fluid is synthetic menstrual liquid without protein having a viscosity of 5.5 cps. The test results are reported in the following table:

| SAMPLE | CAPILLARY PRESSURE (mmHg) |
|---|---|
| Control | 26.2 |
| Invention (sensor of the instrument in contract with side having the 85% binder portion) | 31.8 |
| Invention (sensor of the instrument in contact with side having the 15% binder portion) | 23.5 |

It will be apparent that the capillary pressure, which is a measure of how well the sample transfers liquid to the core of sphagnum moss material, is higher in the case of the invention (side having 85% binder) than the sample. Also note that the liquid-absorbent article according to the invention performs better when the liquid is deposited on the side containing 85% binder than the side containing 15% binder. These results are very surprising and contrary to conventional wisdom that dictates that high binder concentrations reduce the ability of a porous structure to channel liquid.

Figure 3:
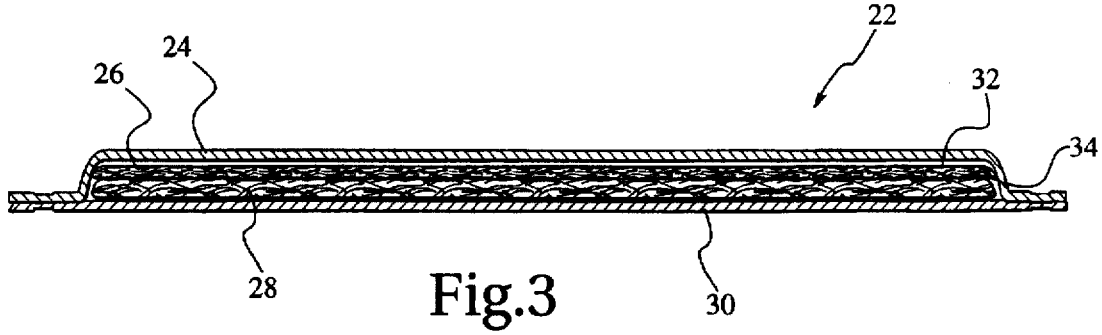
FIG. 3 is a cross-sectional view of a sanitary napkin with the liquid-absorbent article used as transfer layer.

The liquid-absorbent article 10 is well-suited for use as a transfer layer in a sanitary napkin. An example of such sanitary napkin is shown in FIG. 3. The napkin, comprehensively designated by the reference numeral 22, comprises a liquid-permeable cover layer 24 overlaying a transfer layer 26 manufactured in accordance with the invention. Below the transfer layer 26 is provided an absorbent core 28 that preferably includes sphagnum moss material and it is comparatively thin, i.e., having a few millimeters in thickness. Underneath the absorbent core 28 is provided a barrier layer 30 made of liquid-impervious material, such as polyethylene, to prevent liquid entrapped in the absorbent core 30 from egressing the sanitary napkin 22 and staining the wearer's underpants. The cover layer 24 and the barrier layer 30 are joined along their marginal portions so as to form an enclosure that maintains the absorbent core 28 captive. The joint may be made by means of adhesive or heat-bond.

The transfer layer 26 comprises an upper liquid-acquisition surface 32 through which liquid is received from the cover layer 24. The lower surface 34 of the transfer layer that faces the absorbent core 28 is the liquid-release surface through which liquid is passed to the absorbent core. It is preferred to orient the transfer layer 32 in such a way as to place the side containing the most binder up so it forms the liquid-acquisition surface. As discussed earlier, this configuration provides better performance.

Applications of the product and methods of the present invention for sanitary and other health-care uses can be accomplished by any sanitary protection, incontinence, medical and absorbent methods and techniques as are presently or prospectively known to those skilled in the art. Thus, it is intended that the present application covers the modifications and variations of this invention provided that they come within the scope of the appended claims and their equivalents.

I claim:

1. An integrally formed liquid-absorbent article of particulate material including first and second zones in intimate fluid communicative relationship, each zone having a multiplicity of inter-particle interstices admitting passage of liquid, whereby liquid contained in one of said zones is capable of migrating toward the other of said zones, said liquid-absorbent article containing binder, said first zone having a higher average concentration of binder than said second zone;

wherein said liquid absorbent article is in the form of a sheet;

wherein said zones constitute superposed layers of said sheet;

wherein said liquid-absorbent article includes first and second opposite main faces, said first zone including said first main face and second zone including said second main face and wherein said liquid-absorbent article includes a third zone located between said first zone and said second zone, said third zone having a lower density than said first and second zones.

2. An integrally formed liquid-absorbent article as defined in claim 1, wherein said third zone has a lower concentration of binder than said first zone and second zone.

3. An integrally formed liquid-absorbent article as defined in claim 1, wherein said liquid-absorbent article includes fibrous material.

4. An integrally formed liquid-absorbent article as defined in claim 3, wherein said fibrous material is cellulose.

5. An integrally formed liquid-absorbent article as defined in claim 1, wherein said liquid-absorbent article includes binder in the range from about 10% to about 25% by weight of solids in said liquid-absorbent article.

6. An integrally formed liquid-absorbent article as defined in claim 5, wherein said binder is selected in the group consisting of EVA and acrylic.

7. An integrally formed liquid-absorbent article as defined in claim 5, wherein said first zone contains no less than about 75% of a total binder content of said liquid-absorbent article.

8. A transfer layer for a disposable absorbent product comprising the integrally formed liquid-absorbent article of claim 1.

9. A transfer layer for a disposable absorbent article, said transfer layer including particles defining a multiplicity of inter-particle interstices admitting passage of liquid, said transfer layer including a liquid-acquisition surface through which liquid can ingress said transfer layer and a liquid-release surface through which liquid can egress said transfer layer, said transfer layer containing binder, a concentration of binder in a vicinity of one of said surfaces being lower than in a vicinity of the other of said surfaces;

wherein said transfer layer is in the form of a sheet, said surfaces being opposite to one another and forming respective main faces of said sheet;

wherein said transfer layer includes first and second zones forming superposed layers of said sheet, each zone including one of said surfaces, said first zone having a higher concentration of binder than said second zone; and wherein said transfer layer further includes a third zone located between said first zone and said second zone, said third zone having a lower density than said first and second zones.

10. A transfer layer as defined in claim 9, wherein said third zone has a lower concentration of binder than said first zone and second zone.

11. A transfer layer as defined in claim 9, wherein said first zone includes said liquid-acquisition surface and said second zone includes said liquid-release surface.

12. A transfer layer as defined in claim 9, wherein said transfer layer is integrally formed.

13. A transfer layer as defined in claim 9, wherein said transfer layer includes fibrous material.

14. A transfer layer as defined in claim 13, wherein said transfer layer is made of cellulosic fibers.

15. A transfer layer as defined in claim 13, wherein said transfer layer includes binder in the range from about 10% to about 25% by weight of solids in said transfer layer.

16. A transfer layer as defined in claim 15, wherein said binder is selected in the group consisting of EVA and acrylic.

17. A transfer layer as defined in claim 15, wherein said first zone contains no less than about 75% of a total binder content of said transfer layer.

18. A disposable absorbent product including the transfer layer of claim 13.

19. A disposable absorbent product as defined in claim 18, wherein said disposable absorbent product is selected from the group consisting of sanitary napkin, diaper, adult incontinence brief, urinary pad, wound dressing and nursing pad.

* * * * *